United States Patent [19]

Stewart

[11] 4,059,693

[45] Nov. 22, 1977

[54] ANALGESIC ACTION OF SUBSTANCE P

[75] Inventor: John M. Stewart, Denver, Colo.

[73] Assignee: University Patents, Inc., Stamford, Conn.

[21] Appl. No.: 694,974

[22] Filed: June 11, 1976

[51] Int. Cl.$^2$ .................. C07C 103/52; A61K 37/00
[52] U.S. Cl. ............................. 424/177; 260/112.5 R
[58] Field of Search .................. 260/112.5 R; 424/177

[56] References Cited

U.S. PATENT DOCUMENTS

| 3,862,114 | 1/1975 | Scandrett | 424/177 |
|---|---|---|---|
| 3,912,711 | 10/1975 | Leeman et al. | 424/177 |

OTHER PUBLICATIONS

Arch. Pharmacol. 285, 301–313 (1974).
Experientia 18, 297–344 (1962).
Arch. Pharmacol. 281, 233–239 (1974).

*Primary Examiner*—Delbert R. Phillips
*Attorney, Agent, or Firm*—Fidelman, Wolffe & Waldron

[57] ABSTRACT

Substance P, an undecapeptide of mammalian origin, and its analogs containing its essential amino acid sequence, are substantially nonaddictive analgesics when administered to mammals such as humans and other warm-blooded animals by intraperitoneal or intramuscular injection in analgesically effective amounts.

4 Claims, No Drawings

ANALGESIC ACTION OF SUBSTANCE P

BACKGROUND OF THE INVENTION

The present invention relates to a method of the production of analgesia in humans and other warm-blooded animals in need of such therapy which comprises administering an amount effective to produce analgesia of Substance P or an analog thereof which contains the essential amino acid sequence of Substance P, and to pharmaceutical preparations adapted for the administration of said compounds.

Substance P is a polypeptide of mammalian origin discovered by Von Euler and Gaddum, J. Physiol. 72, 74 (1931) in extracts of equine brain and intestinal tissue; it was subsequently isolated from cattle brain by Zuber and Jaques, Angew. Chemie (Int. Ed.) 1, 160 (1962). It is known to be a sensory-transmitter substance and a mediator in inhibitory processes.

The amino acid sequence of Substance P is H-Arg-Pro-Lys-Pro-Gln-Gln-Phe-Phe-Gly-Leu-Met-NH$_2$.

Substance P was isolated from bovine hypothalamus by Chang and Leeman, J. Biol. Chem. 245, 4784 (1970), who observed that the crude substance was sialogogic, i.e. it stimulated salivary secretion when injected into anaesthetized rats. The purified substance exhibited similar activity, and was found to exert an effect on smooth muscle and to lower blood pressure and to act as a vasodilator in mammals.

Substance P has been synthesized and is commercially available. Its synthesis is disclosed in Leeman et al. U.S. Pat. No. 3,912,711. The preparation of various analogs of Substance P is described in Scandrett U.S. Pat. No. 3,862,114.

Substance P is known to affect the mammalian central nervous system, but its observed pharmacological action has been confined to its sialogogic and hypotensive activity, and its property of producing intestinal contractions.

GENERAL DESCRIPTION OF THE INVENTION

In accordance with the present invention, Substance P has been found, surprisingly and unexpectedly, to exhibit analgesic properties when administered to mammals, but at the same time, Substance P and its analogs have proved to be substantially nonaddictive. This represents an advance of importance, inasmuch as the only analgesics heretofore known have been opium derivatives or synthetic compounds closely related thereto structurally, all of which are addictive, usually in proportion to their analgesic potency.

Thus, morphine, the most important alkaloid of opium, and its salts, of which the sulfate is the form most commonly employed, produces drug dependence in humans and other animals, and may be attended with undesirable side-effects, such as vomiting, constipation, allergic reactions, and respiratory depression.

Taking morphine sulfate as a standard of reference, Substance P has proved to be not only nonaddictive, but to be about 450 times as potent as an analgesic, and relatively free from significant side-effects.

The analgesic action of Substance P and its analogs which was not known heretofore, is all the more surprising and unexpected because the literature had reported Substance P to be a very potent algogen (pain-producing substance) in the human blister base assay test. Thus investigators were guided away from any consideration of studying pain alleviation by this substance. This may possibly be explained by the fact that whatever pain investigation was done with Substance P utilized the isolated compound, which was not pure and probably contaminated by kinin-like compounds such as bradykinin, which is an extremely potent algogen.

Without wishing to be bound by any particular theory, a possible explanation of the analgesic action of Substance P may lie in the fact that, just as the analgesic action of morphine is exercised through the central nervous system (CNS) so as to alter responses to painful stimuli, Substance P appears to act similarly, but far more efficiently.

It is a generally accepted pharmacologic principle that drugs act on cells by combining with sites on the cell membranes designed to interact with them specifically. Such sites are called receptors. After the drug, or endogenous substance, usually referred to as the agonist, combines with receptor, the cell responds by providing the result induced by the agonist. An example is the uptake of glucose into the muscle cells when they are stimulated by the combining of insulin with the cell receptors. Morphine, or its sulfate, is believed to act on the brain of a mammal by finding in the brain, receptors specific for it, thereby producing the analgesic effect. It is hypothesized that there must be in the brain some endogenous morphine-like substance for which these specific receptors were designed, and the normal function of which is to modulate pain response. The term endorphine has been proposed for this endogenous morphine substance. The evidence suggests that there is such a substance and that it is peptide in character.

The criteria for an endorphine substance are that it is active in MS (morphine sulfate) assays, and that it combines with so-called MS-receptors in brain tissue. In both these actions it must be antagonized by a specific MS antagonist; the one generally used is naloxone (1-N-allyl-7,8-dihydro-14-hydroxynormorphinone), described in U.S. Pat. No. 3,254,088, a modification of the morphine structure which combines with MS-receptors but does not stimulate the cells to inhibit pain responses. The most widely accepted MS assay is the field-stimulated guinea pig illeum, which involves the action of MS on intestine. In the ileum assay the electrically induced contractions are inhibited by MS or endorphine, and both inhibitions are antagonized by naloxone (Nal). For the receptor assays, brain membrane particles are used. Radioactive MS combines with the particles, and is displaced by naloxone; endorphine also displaces MS, and its binding is inhibited by naloxone.

The first definite substances with endorphine activity were described by Hughes et al., Nature, 258, 577-9 (1975), as being two pentapeptides isolated from brain. They were: Tyr-Gly-Gly-Phe-Met, called Methionine-Enkephalin (Met-Enk), and Tyr-Gly-Gly-Phe-Leu, called Leucine-Enkephalin, the former being the more potent. Its structure was recognized as being contained within the amino acid sequence of an anterior pituitary hormone, β-lipotropin (LPH), wherein it constituted residues 61-65 of that 91-amino acid peptide hormone. It was later established that Met-Enk does not exhibit significant analgesic activity in vivo.

Smyth, 14th European Peptide Symposium, April 11-17, 1976, reported that the entire 61-91 LPH fragment, which he named Lipotropin C-Fragment, extracted from pig pituitary, was found to inhibit the binding of naloxone and dihydromorphine to brain opiate receptor, with a potency approximately thirty times that of methionine enkephalin in vitro. These known peptides all contained the amino acid sequence Tyr-Gly-Gly-Phe, which does not, however, occur in Substance P.

Hence the analgesic activity of Substance P or its analogs, could not have been predicted from any structural resemblance. Substance P, as mentioned previously, is an undecapeptide and possesses the sequence: $H_2N$-Arg-Pro-Lys-Pro-Gln-Gln-Phe-Phe-Gly-Leu-Met-$CONH_2$. In its pure or synthetic form it has a molecular weight of 1347. It is likely that Substance P operates on a different type of cell receptor than the Enk-related pentapeptides. This difference in analgesic action may be due to the fact that the amino acid tyrosine (Tyr) is not present in the structure of Substance P, while it must be present at the amino-terminus of Enk-peptides, and must possess a free amino group. Tyrosine ($\beta$-(p-hydroxyphenyl)alanine), possesses a phenolic group. Substance P has no phenolic group or any other hydroxy group, being thereby further distinguished in its structure and mode of action from the Enk-peptides.

In accordance with the invention, Substance P or its analogs containing its essential amino acid sequence, may be employed in purified natural or synthetic form, the latter being preferred because of availability and consistency of composition.

Natural Substance P is obtained from frozen bovine brain tissue by homogenizing in acetone-dilute HCl, and removing lipid from the extract with petroleum. After evaporation of the solvent, the residual material is chromatographed successively by: (1) gel chromatography on Sephadex G-25; (2) ion exchange chromatography on sulfoethyl-Sephadex G-25; (3) ion exchange chromatography on carboxymethylcellulose. Following chromatography, the final purification is by means of preparative paper electrophoresis at pH 3. This procedure yields a homogeneous material.

The Substance P may be employed in the form of the free amide, or that of a salt of a pharmaceutically acceptable acid, which may be either inorganic or organic. Examples of suitable inorganic acids include hydrochloric, sulfuric, and phosphoric acids, while those of suitable organic acids are carboxylic acids having from 2 to 18 carbon atoms, preferably lower aliphatic carboxylic acids, such as acetic, propionic, butyric, valeric, and capric acids, but also including decanoic, undecanoic, lauric, myristic, oleic, palmitic, and stearic acids. The acetate is preferred.

Specific forms of parenteral administration are employed, in accordance with the invention, those modes of administration being chosen which will minimize the hypotensive action of Substance P. The modes of administration which are advantageously used include intraperiteonal, which is presently preferred, as well as intramuscular, intracerebral (for animals), or peripheral modes, such as intravenously in the tail vein in the case of animals, such as rats, mice, or rabbits.

The most favorable administration route and dosage rate will depend upon the subject and the mode of administration.

The dosage rate is selected so as to provide analgesia for a useful minimum period of time, while at the same time avoiding any impact of sudden severe lowering of blood pressure. It has been found that in this way analgesia can be produced in test animals which commences in about 20–30 minutes following administration, reaches its peak effectiveness in about 1.5 hours, and continues for a total of about 2 to 2.5 hours or even longer. In contrast thereto, the intravenous administration described in the prior art produces a sharp lowering of blood pressure almost immediately, but this does not ordinarily last for more than about 7 minutes.

The Substance P or its salts may be administered, in accordance with the invention, alone, or in association with a pharmaceutically acceptable carrier suitable for the aforementioned types of parenteral administration. The injectable preparations may be solutions or suspensions in sterile, preferably pyrogen-free, water or in a suitable oil as a carrier, Examples of such oils are pharmaceutically acceptable vegetable oils, commonly employed for this purpose, such as peanut, sesame, olive or caster oil.

In order to obtain a prolonged action or sustained release effect, the active ingredient may be injected in depot form, in suspension in a pharmaceutically acceptable fatty or waxy vehicle which melts at approximately body temperature of mammals, including humans and other warm blooded animals.

The unit dosage, depending upon the mammal, may range from about 0.1 to about 50 micrograms per kg of body weight. Thus the mode of administration contemplated according to the invention permits of dosages much higher than would be permissible using intravenous administration, which latter method would produce excessive hypotension.

DESCRIPTION OF THE PREFERRED EMBODIMENT

The following examples illustrate the practice of the invention, but are not to be regarded as limiting:

EXAMPLE 1

Injectable Preparation of Substance P

A stock solution was prepared by dissolving 200 micrograms of Substance P (synthetic) in 0.6 ml of 0.1 N acetic acid and physiological saline (0.9% NaCl). Prior to injection this was diluted with saline in a 1:10 ratio. The injection volume used in mice was 0.04 ml of diluted preparation.

EXAMPLE 2

Analgesic Action of Substance P in Mice

The drug was administered by intraperitoneal injection, employing the solution prepared according to Example 1. Three groups of mice, 5 animals per group, received a single injection ip of Substance P or vehicle alone. Mice weighed 30 grams each. Group 1: Substance P, 5 microgram per mouse ($5 \times 10^{-9}$g)(0.167 microgram/kg) Group 2: Substance P, 1 microgram per mouse ($1 \times 10^{-6}$g)(33.3 microgram/kg) Group 3: Vehicle alone On the day before the animals were to be given the drug, each animal was tested on the hot plate analgesiometer for its reaction time (the time in seconds after placing on the hot plate until the animal jumps). The next day animals were given the injection and then tested on the analgesiometer at times of 30, 60, 90, 120 and 150 minutes after the injection. From the reaction times observed the control reaction time determined the previous day was subtracted. The reaction times given in the table below are the increase in reaction time (over the control value) due to the injection.

| Time of | Reaction Time Over Controls | | |
|---------|---------|---------|---------|
| Testing | Group 1 | Group 2 | Group 3 |
| 30 min. | 7.04 ± 1.91 | 7.6 ± 2.68 | 0.3 ± 1.48 sec |
| 60 | 6.56 ± 2.4 | 11.44 ± 3.49 | 2.08 ± 1.48 |
| 90 | 8.36 ± 3.2 | 10.96 ± 1.33 | 1.12 ± 1.41 |
| 120 | 6.24 ± 1.4 | 8.2 ± 3.18 | 3.0 ± 0.86 |
| 150 | 3.84 ± 2.12 | 4.08 ± 1.26 | 2.32 ± 1.20 |

At all times except 150 min, the increases in reaction times of the animals in groups 1 and 2 were significant (p less than 0.05 in the Student t test) compared to the vehicle controls (Group 3). The reaction time increases at 150 min were not statistically significant, due to the small number of animals used and the fact that the analgesia was wearing off at that time.

EXAMPLE 3

Analgesic Action of Substance P in Mice

The drug (SP) was administered by intracerebral injection, using an injection volume of 0.04 ml, using the technique described by Haley, et al. Brit. J. Pharmacol. 12, 12 (1957). Morphine (MS) and naloxone (N) was prepared in physiological saline (0.9% NaCl). Control solutions were physiological saline or 0.01 N acetic acid in physiological saline. Male Swiss Webster mice were used.

The acute effects of SP, MS, SP plus N, and MS plus N on pain were tested using the hot plate technique described in Example 2. At the beginning each mouse's reaction time on the hot plate was measured (RT), the drugs were then injected, the RT measured at 30 minute intervals, the first measurement being made 30 minures after administration. Analgesia is reflected by an increased reaction time, whereas tolerance is reflected by a shortened reaction time or a return to a normal RT. After administration of SP the reaction times were significantly increased compared to those of controls. With naloxone, when 0.06 mg/mouse was injected intraperitoneally immediately before the intracerebral injection of SP or MS, the reaction times were not increased during the first measurement, but gradually became longer.

EXAMPLE 4

50 ng of Substance P was administered peripherally to mice by intravenous injection in the tail vein. The mean reaction time at 90 minutes was 6.2 seconds.

What is claimed is:

1. Method for the production of analgesia in mammals requiring such therapy which comprises administering by injection an amount of effective to produce analgesia within the range of about 0.1 to about 50 micrograms per kg. of body weight of a compound selected from the group consisting of Substance P, and salts thereof of a pharmaceutically acceptable acid.

2. The method of claim 1 in which the active ingredient is Substance P.

3. A pharmaceutical preparation in unit dosage form adapted for administration to a mammal by injection to produce analgesia, comprising, per dosage unit, as its active ingredient an effective amount within the range of about 0.1 to about 50 micrograms of a compound selected from the group consisting of Substance P and salts thereof of a pharmaceutically acceptable acid, and a pharmaceutical diluent.

4. The preparation of claim 3 in which the active ingredient is Substance P.

* * * * *